United States Patent [19]
Hasegawa et al.

[11] Patent Number: 5,346,984
[45] Date of Patent: Sep. 13, 1994

[54] STAR-SHAPED NYLONS, METHODS FOR THEIR PREPARATION, TETRASUBSTITUTED CARBOXYLIC ACIDS AND METHODS FOR THEIR PREPARATION

[75] Inventors: Naoki Hasegawa; Arimitsu Usuki; Akane Okada; Toshio Kurauchi, all of Aichi, Japan

[73] Assignee: Kabushiki Kaisha Toyota Chuo Kenkyusho, Aichi, Japan

[21] Appl. No.: 46,837

[22] Filed: Apr. 14, 1993

[30] Foreign Application Priority Data

Apr. 14, 1992 [JP] Japan .................................. 4-121310
Feb. 26, 1993 [JP] Japan .................................. 5-062896

[51] Int. Cl.$^5$ ........................ C08G 69/08; C08G 69/14
[52] U.S. Cl. ........................................ 528/323; 528/9; 528/228; 528/310; 528/327
[58] Field of Search ................... 528/310, 327, 228, 9

[56] References Cited
U.S. PATENT DOCUMENTS 3,549,601 12/1970 Fowell ................................ 528/323
4,075,271 2/1978 Lofquist et al. ..................... 528/323
4,599,400 7/1986 Tomalia et al. .
4,650,608 3/1987 Takeo et al. ........................ 528/323

OTHER PUBLICATIONS

American Chemical Society, Jun. 1989, 30(1), pp. 117–118, J. A. Warakomski, "Polymer Preprints".

*Primary Examiner*—John Kight, III
*Assistant Examiner*—P. Hampton-Hightower
*Attorney, Agent, or Firm*—Oblon, Spivak, McClelland, Maier & Neustadt

[57] ABSTRACT

Star-shaped nylons with low melt viscosities and excellent mechanical properties, methods for their preparation, a novel tetrasubstituted carboxylic acid for use as a polymerization core therefor and methods for its preparation are provided.

A star-shaped nylon has polymer chains emanating from 3 or more polymerization initiation groups which are substituents bonded to every other or more separated carbon atoms on an aromatic ring of an aromatic compound. The star-shaped nylon is produced by homogeneously mixing the aromatic compound with molten nylon monomer and polymerizing the nylon monomer with the respective polymerization initiation groups as the starting points. A novel tetrasubstituted carboxylic acid having a structure of 3,5,3',5'-biphenyltetracarboxylic acid is useful as a polymerization core for star-shaped nylons.

17 Claims, 2 Drawing Sheets

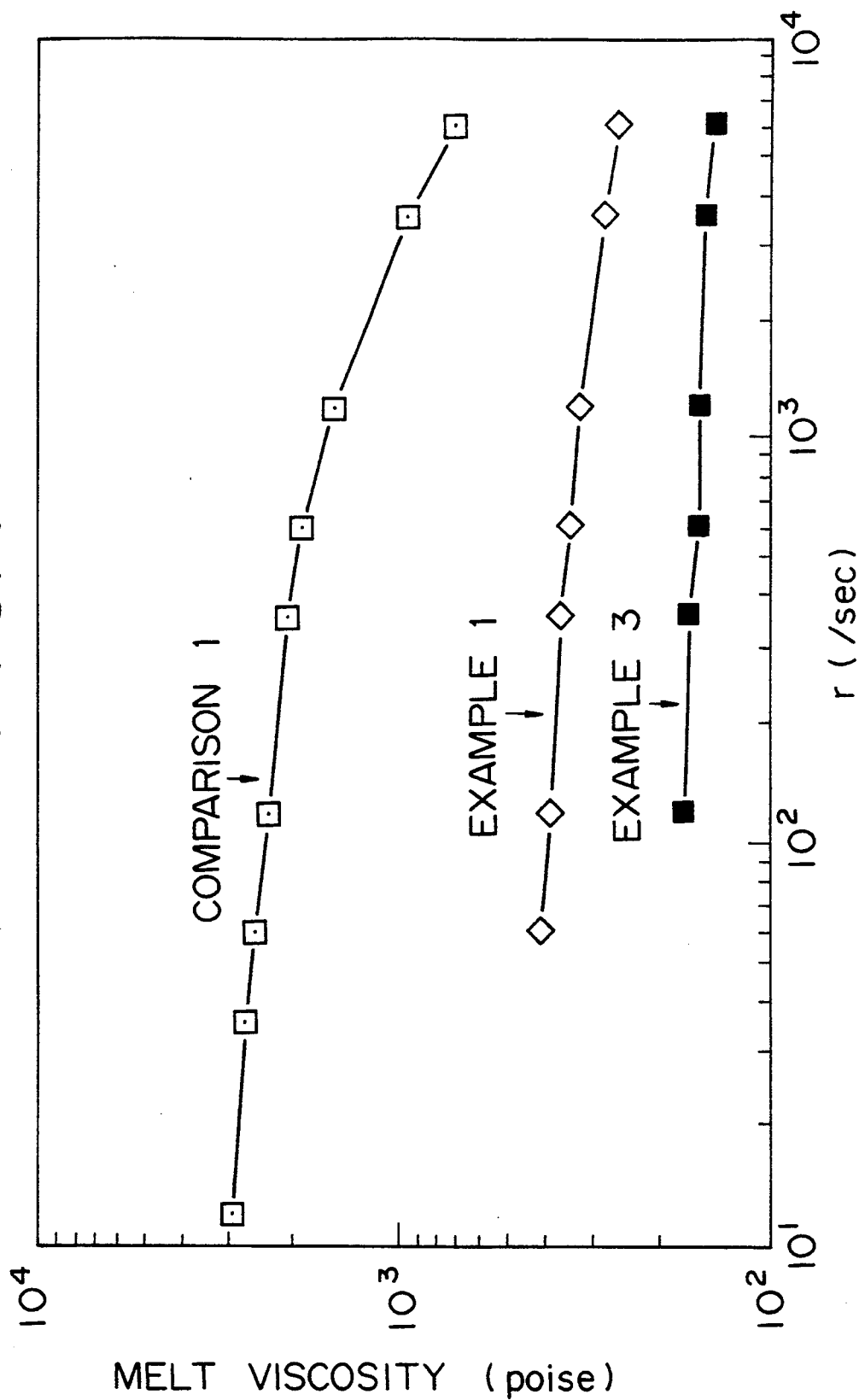

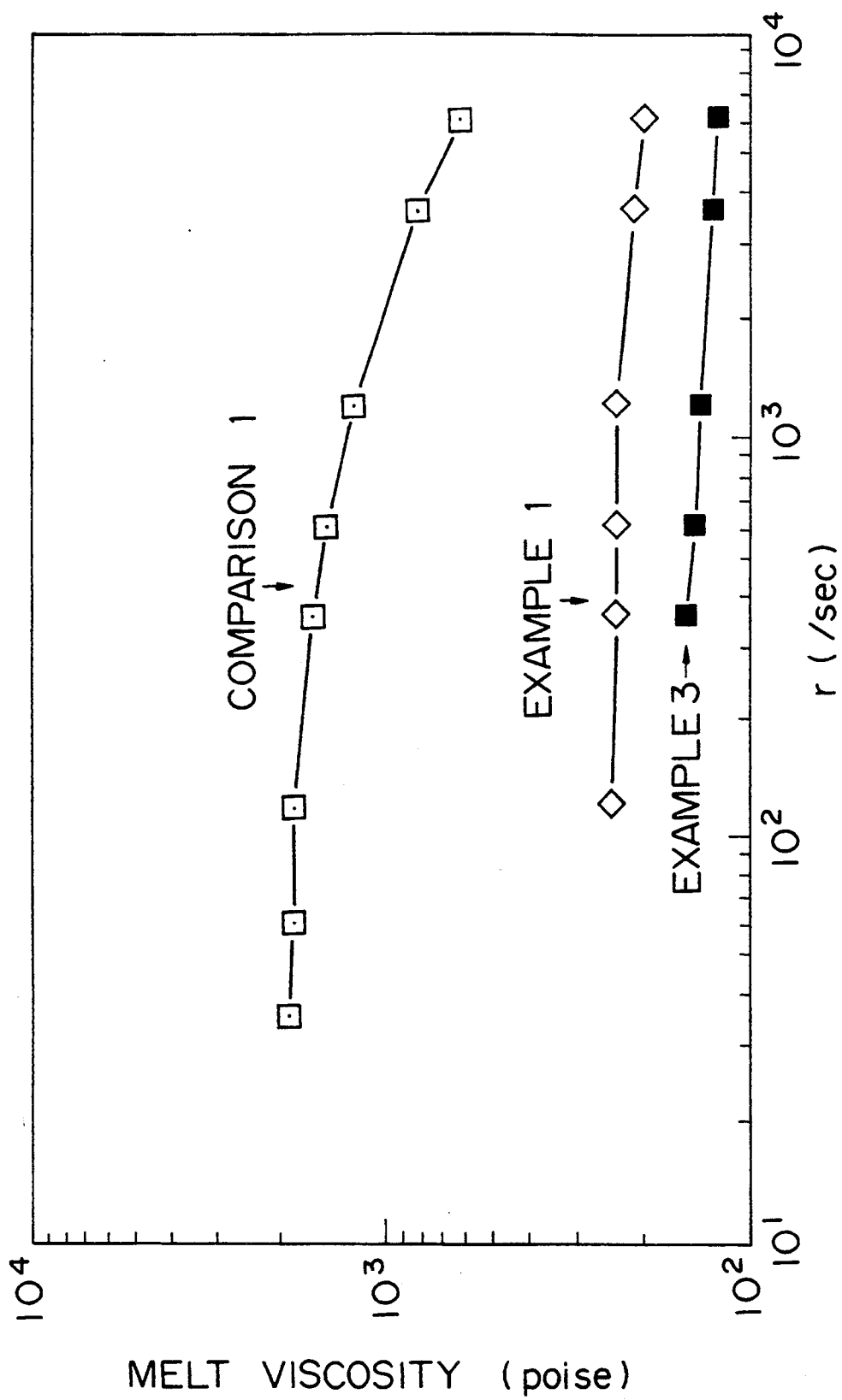

STAR-SHAPED NYLONS, METHODS FOR THEIR PREPARATION, TETRASUBSTITUTED CARBOXYLIC ACIDS AND METHODS FOR THEIR PREPARATION

BACKGROUND OF THE INVENTION

1. Field of the Invention

The present invention relates to star-shaped nylons, methods for their preparation, tetrasubstituted carboxylic acids and methods for their preparation. More particularly, it is concerned with star-shaped nylons with desired properties provided by use of characteristic polymerization cores, new tetrasubstituted carboxylic acids for use as the aforementioned polymerization cores and methods for their preparation.

2. Description of the Related Art

The so-called star-shaped polymers are macro molecules of a structure where a plurality of radial polymer chains emanate from a polymerization core as a center, their chemical structure being characterized in that, as compared with the conventional linear polymers, the molecular weight per polymer chain is less, and the respective polymer chains combine with each other through the polymerization core. Therefore, star-shaped polymers have relatively less entanglement of respective polymer chains, which contributes to their relatively low melt viscosities. This often leads to their preferable physical properties to enable injection molding into films, or leads to excellent compatibility with other polymers to broaden the possibilities of polymer blends.

Also relating to nylons, those of star-shaped type have been investigated as exemplified in U.S. Pat. No. 4,599,400 and "Polymer Preprints," 30(1), pp117-118, American Chemical Society, 1989. For example, a star-shaped nylon 6 is described therein which is prepared by making use of a star-shaped amine compound with plural amino groups on separate positions in a molecule as a polymerization core, and subjecting the respective amino groups to ring-opening polymerization with ε-caprolactam or a nylon monomer.

The above-mentioned type of star-shaped nylon, however, does not always exhibit low melt viscosity, nor good mechanical properties (e.g. tensile strength, tensile modulus, etc.). These drawbacks are assumed to be due to the following causes characteristic of nylons.

That is, polymer chains of nylon contain numerous amide bond (—CO—NH—) portions which are indispensable to crystallization due to formation of hydrogen bonds between nylon molecules upon solidification, and eventually contribute to improvement in various mechanical properties of nylon materials.

In the early stage of polymerization for star-shaped nylons, however, the respective polymer chains in the same molecule are present in close vicinity to each other near the polymerization core, and further the reactivity of the amide bond portions of the respective polymer chains remain high until completion of polymerization. So the mutual contact of the respective polymer chains in the same molecule causes radical formation due to deprotonation at the amide bond portions and thus formation of intramolecular network structure among the polymer chains. Such intramolecular network structure is known to cause an increase in melt viscosity of nylon.

The intramolecular network structure formed between the amide bond portions prevents formation of hydrogen bonds among nylon molecules caused by amide bonds upon the solidification, resulting in poor crystallization which provides nylon materials with inferior mechanical properties.

For the foregoing reasons, it is necessary to keep the respective polymer chains in the molecule from their mutual close contact in the early stage of polymerization in order to prepare star-shaped nylons having low melt viscosities and excellent mechanical properties.

According to the prior art, however, a star-shaped amine compound as a polymerization core is not of a rigid molecular structure, and eventually infallible separation of the respective polymer chains from each other cannot be attained in the course of polymerization, thereby failing to prevent formation of the intramolecular network structure discussed above, even if a plurality of amino groups are positioned separated from each other in the molecule so that the respective polymer chains in the molecule do not mutually contact.

SUMMARY OF THE INVENTION

Accordingly, an object of the present invention is to provide star-shaped nylons with low melt viscosities and excellent mechanical properties due to no formation of the aforementioned intramolecular network structure upon polymerization of nylon monomers and due to satisfactory crystallization upon solidification, and processes for preparations thereof. Another object of the present invention resides in a plentiful supply of types of polymerization cores which enable the provision of the star-shaped nylons mentioned above.

In a first aspect, the present invention provides a star-shaped nylon with nylon polymer chains emanating from 3 or more polymerization initiation groups which are substituents bonded to every other or more separated carbon atoms on the aromatic ring of an aromatic compound.

In a second aspect, the present invention provides a process for the preparation of a star-shaped nylon, which comprises: preparing an aromatic compound substituted with 3 or more polymerization initiation groups for nylon monomers, which are bonded to every other or more separated carbon atoms on an aromatic ring of an aromatic compound; homogeneously mixing the aromatic compound with molten nylon monomers under a condition where no other polymerization initiators for nylon monomers are present; and polymerizing the nylon monomer starting from the respective polymerization initiation groups of the aromatic compound mentioned above.

According to the aforementioned first and second aspects, an aromatic compound of rigid molecular structure is employed as the polymerization core for a star-shaped nylon, and polymerization initiation groups as substituents are bonded to every other or more separated carbon atoms on an aromatic ring of an aromatic compound, so that the polymerization core functions as an effective spacer to place the respective polymer chains in the same molecule for scarce mutual contact thereof early in the course of polymerization for nylon.

Therefore, no formation is performed of intramolecular network structure between amide bond portions during the polymerization for star-shaped nylons, leading to promotion of formation of intramolecular hydrogen bonds upon solidification with satisfactory crystallization.

Here, aromatic rings of aromatic compounds are in a form of flat hexagonal plates or more complicated polygonal plates, and thus, at solidification after the completion of polymerization, these plate-like aromatic rings tend to be oriented in a pile in the perpendicular thereof. For this reason, the respective polymer chains of star-shaped nylon molecules also have a tendency to be oriented horizontally among the molecules, thus promoting more efficient formation of intermolecular hydrogen bonds.

Next, the polymerization core of a star-shaped nylon according to the present invention, which bears 3 or more polymerization initiation groups, has a lower molecular weight per polymer chain than conventional linear polymers, and maintains a structural characteristic peculiar to star-shaped polymers in that the respective polymer chains combine with each other through the polymerization core.

In addition, in the method for the preparation of star-shaped nylons according to the second aspect, an aromatic compound as a polymerization core is homogeneously mixed with molten nylon monomers under a condition where no other polymerization initiators for nylon monomers are present, and then the nylon monomers are subjected to polymerization starting from each of the polymerization initiation groups of the abovementioned compound. Accordingly, the physical properties cannot be spoiled due to formation of linear nylon molecules which may be produced because of the presence of other types of polymerization initiator for nylon monomers.

The aforementioned aspects contribute to the provision of star-shaped nylons with low melt viscosities and various excellent mechanical properties. In this connection, star-shaped nylons are of structure constructed by combining polymer chains, which are shorter than those of linear nylons, through a polymerization core, which structure causes an increase in glass transition temperature, an index of thermal stability.

The third aspect of the present invention resides in tetrasubstituted carboxylic acids of chemical structure generically named 3,5,3',5'-biphenyltetracarboxylic acids according to the nomenclature of International Union of Pure and Applied Chemistry (IUPAC). The chemical structure of this tetrasubstituted carboxylic acid is represented by Formula 1 given below.

Formula 1:

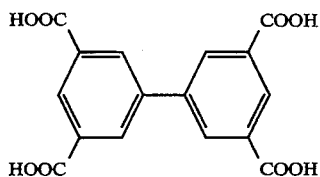

Tetrasubstituted carboxylic acid, which has 4 polymerization initiation groups (carboxyl groups) as substituents bonded to every other or more separated carbon atoms on an aromatic ring (biphenyl ring) of an aromatic compound, is a novel compound which may be used as the polymerization core in the first and second aspects of the present invention.

In a fourth aspect, the present invention provides a method for the preparation of the tetrasubstituted carboxylic acid, which comprises dissolving a 1,3-dicarboxy 5-halobenzene in a solvent, followed by dehalogenation condensation in the presence of a catalyst of metal belonging to group X of the periodic table.

This method for the preparation of the tetrasubstituted carboxylic acid serves to produce tetrasubstituted carboxylic acid according to the third aspect.

Usually, the preparation of tetrasubstituted carboxylic acids involves coupling of 5-diazonium salts of 1,3-dicarboxybenzene with copper or the like. The following of this process by the present inventors, however, led to the synthesis of the diazo compound represented by Formula 2 shown below, but not to the synthesis of the tetrasubstituted carboxylic acid according to the third aspect. Considering this fact, the present inventors undertook the multi-faceted research on synthesis methods, resulting in the completion of a method for the preparation of the tetrasubstituted carboxylic acid according to the fourth aspect.

Formula 2:

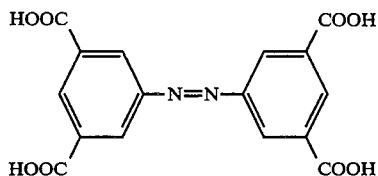

BRIEF DESCRIPTION OF THE DRAWINGS

FIG. 1 is a graph showing the results of measurement of melt viscosities at 230° C. of nylon resins of Example 1, Example 3 and Comparison 1.

FIG. 2 is a graph showing the results of measurement of melt viscosities at 240° C. of nylon resins of Example 1, Example 3 and Comparison 1.

DETAILED DESCRIPTION OF THE INVENTION

Hereunder, the first to fourth aspects of the present invention will be explained in detail.

The aromatic compounds used in the present invention include all compounds with an aromatic ring and their derivatives in general.

The aromatic ring includes benzene ring, naphthalene ring, anthracene ring, etc., and further heterocycles such as pyridine ring, pyrrole ring, indole ring, furane ring, thiophene ring, purine ring, quinoline ring, phenanthrene ring, porphyrin ring, phthalocyanine ring, naphthalocyanine ring and the like.

Particularly, porphyrin ring, phthalocyanine ring and naphthalocyanine ring are of large cyclic structure which is expected to provide a general advantage in that, as compared with benzene ring or the like, more polymerization initiation groups as substituents may be bonded to every other or more separated carbon atoms on an aromatic ring.

The skeleton of the aromatic compounds of the present invention may consist only of any one of the various aromatic rings discussed above and their condensed rings, and further it can be composed of biphenyl, triphenyl, bipyridine, etc., i.e. 2 or more aromatic rings combined without condensation. In addition, the structure may be such that, between the 2 or more aromatic rings there exists a portion comprising an alkylene group, allylene group, arylene group, diazo group, carbonyl group, ether group, amido group, ester group, amino group or the like.

In the aromatic compounds according to the present invention, a hydrogen atom may bond to the carbon atoms on an aromatic ring, to which no polymerization initiation groups bond, or a variety of groups not capable of preventing the preparation of a star-shaped nylon may be bonded thereto as substituents.

For the aromatic compounds according to the present invention, the most suitable polymerization initiation group is amino or carboxyl group, but other polymerization initiation groups may be used which can initiate polymerization for nylon monomers.

Preferably, the aforementioned polymerization initiation groups as substituents bond to every other or more distant or separated carbon atoms on an aromatic ring of an aromatic compound. This is because bonding to carbon atoms at neighboring positions on the aromatic ring not only causes formation of the aforementioned intramolecular network of polymer chains, but also is apt to induce so-called steric hindrance or a side reaction such as imide cyclization between the polymerization initiation groups, thus failing to produce a star-shaped nylon with desired physical properties.

In addition, preferably, the aromatic compounds may be substituted with 3 or more polymerization initiation groups, because substitution of the aromatic compounds with only 1 or 2 polymerization initiation groups results in the formation of 1 or 2 polymerization chains emanating therefrom, thereby producing nylon molecules in a linear state rather than in a star-shape when viewed as a whole. More preferably, the aromatic compounds have not less than 3, but not more than 10 polymerization initiation groups as substituents, for the reason that the presence of 10 or more polymerization initiation groups leads to the production of 10 or more intramolecular polymer chains, which may cause a jam of intramolecular polymer chains around the core of the star-shaped nylon, which should be undesirable in view of the above-mentioned intramolecular network or crystallization properties.

The polymerization initiation groups do not necessarily bond directly to the carbon atoms on the aromatic ring, and may bond thereto through certain intermediate structural portions. Such intermediate structural portions include an alkylene group, allylene group, arylene group, etc. and in effect any intermediate structural portion may be utilized so long as it hinders neither the action of the polymerization initiation groups to initiate the polymerization nor that of the polymerization core to separate the intramolecular polymer chains in the molecule.

Several typical examples of such polymerization cores are illustrated hereunder.
1,3,5-benzenetricarboxylic acid (trimesic acid);
3,5,3',5'-biphenyltetracarboxylic acid;
2,4,6-pyridinetricarboxylic acid;
3,5,3',5'-bipyridyltetracarboxylic acid;
1,3,5,7-naphthalenetetracarboxylic acid;
1,3,6,8-acridinetetracarboxylic acid;
3,5,3',5'-benzophenonetetracarboxylic acid;
1,3,5-triaminobenzene;
1,3,5-tri(aminomethyl)benzene;
3,5,3',5'-tetraaminobiphenyl;
2,4,6-triaminopyridine;
3,5,3,',5'-tetraaminobipyridine;
1,3,5,7-tetraaminoaphthalene;
1,3,6,8-tetraaminoacridine; and
3,5,3',5'-tetraaminobenzophenone.

Typical examples of porphyrin polymerization cores are tetrakis(carboxyphenyl)porphyrin represented by Formula 3, aluminum tetrakis(carboxypenyl)porphyrin, titanium tetrakis(carboxyphenyl)porphyrin, nickel tetrakis (carboxyphenyl) porphyrin, rhodium tetrakis(carboxyphenyl)porphyrin, etc.

Formula 3:

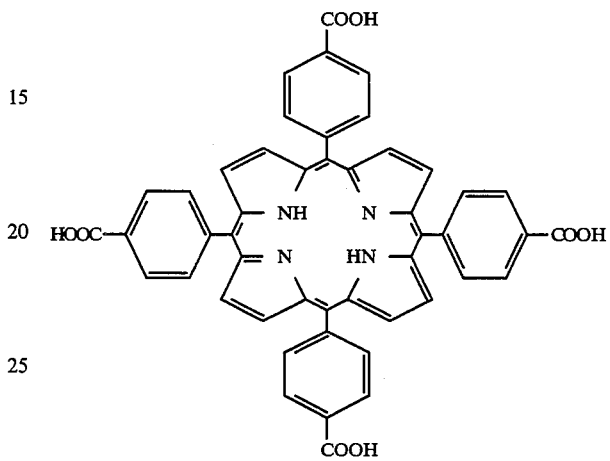

Typical examples of phthalocyanine polymerization cores are tetracarboxyphthalocyanine represented by Formula 4, chloro(tetracarboxyphthalocyaninate)aluminum, (tetracarboxyphthalocyaninate)cobalt, (tetracarboxyphthalocyaninate)copper, and (tetracarboxyphthalocyaninate) nickel represented by Formula 5, (tetracarboxyphthalocyaninate)iron, (tetracarboxyphthalocyaninate)oxovanadium, (tetracarboxyphthalocyaninate)lead, (tetracarboxyphthalocyaninate)magnesium, (tetracarboxyphthalocyaninate)tin, (tetracarboxyphthalocyaninate)zinc, etc.

Formula 4:

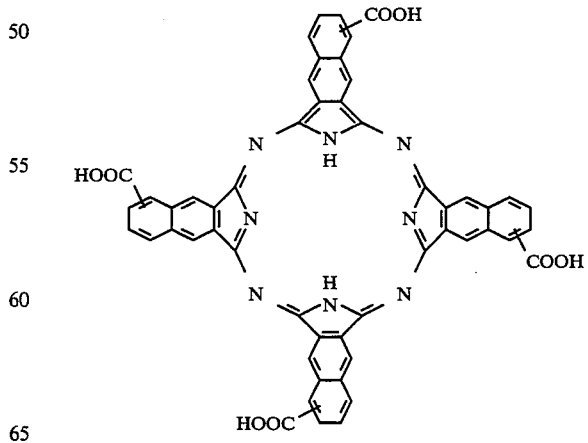

Formula 5:

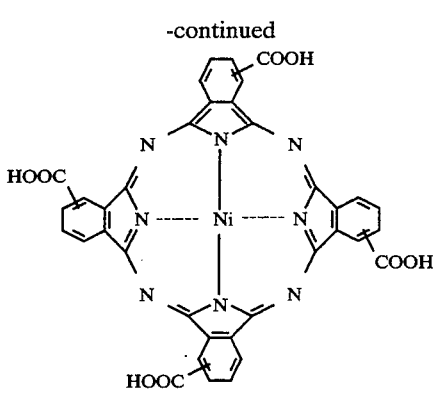

Typical examples of naphthalocyanine polymerization cores are tetracarboxynaphthalocyanine represented by Formula 6, metallic tetracarboxynaphthalocyanine represented by Formula 7 (wherein M is a metal atom).

Formula 6:

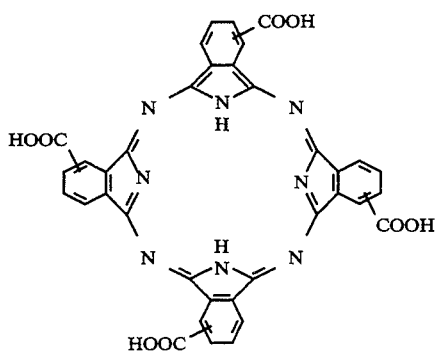

Formula 7:

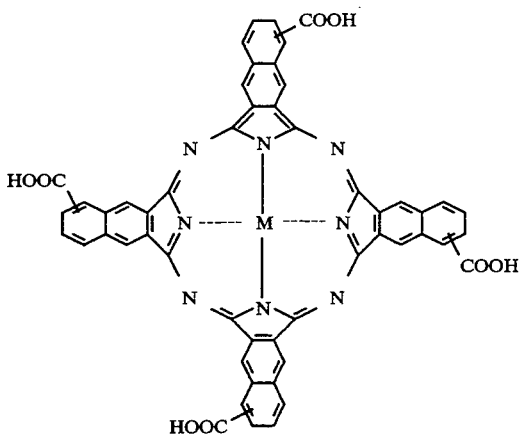

The nylon monomers are not particularly limited. Preferably, nylon monomers such as valerolactam, caprolactam, 2-azacyclododecanone, 2-azacyclotridecanone (laurolactam), 1,8-diazacyclotetradecane-2,7-dione, etc. are employed.

The conventional polymerization for nylons is often carried out in the presence of water or a small amount of acid. However, as the co-presence of water or acid capable of initiating polymerization causes formation of linear nylons, water, acid or other polymerization initiators must be substantially excluded prior to the polymerization for nylons according to the preparation method of the present invention.

The process for the polymerization for nylons is preferred to be conducted under vacuum (desirably, under reduced pressure of around $10^{-2}$ Torr). This is because the water and oxygen contained in the reactive materials may be excluded under vacuum. Further, it is preferred that the process for the polymerization for nylons is carried out in a sealed tube. This is because the polymerization reaction of star-shaped nylons does not always proceed readily, and thus it becomes necessary to prevent evaporation of volatile nylon monomers during the progress of the reaction.

The molecular weight per polymer chain of the star-shaped nylon depends on the ratio of the number of the polymerization initiation groups on the polymerization core to the amount of the nylon monomer charged. For example, to state simply, around 100-mers are synthesized if 100 molecules of nylon monomer is used per polymerization initiation group. The molecular weight of the star-shaped nylons according to the present invention is not particularly limited; but, the number average molecular weight Mn is prefereably controlled in the range of 5,000–50,000, most preferably, in the range of 10,000–30,000 for better mechanical properties and lower melt viscosity.

The above-mentioned molecular weight is of the entire star-shaped nylon, and the molecular weight per polymer chain in the molecule almost equals the value calculated by dividing the total molecular weight by the number of the polymer chains.

In the fourth aspect of the present invention, the halogen in 1,3-dicarboxy-5-halobenzene is preferred to be bromine, but other halogens such as iodine, chlorine and fluorine may be used as well.

Palladium, nickel or platinum, which belong to group X of the periodic table, may be used as the metallic catalyst for dehalogenation condensation of the 1,3-dicarboxy-5-halobenzene.

In order to bring about the dehalogenation condensation, it is necessary to keep the 1,3-dicarboxy-5-halo benzene in solution, preferably in an aqueous solvent in order to maintain the activity of the aforementioned catalyst. Most desirably, the 1,3-dicarboxy-5-halobenzene is treated with an alkali such as caustic soda to convert its 2 carboxylic groups to an alkaline salt thereby, imparting water-solubility to the compound.

To simplify the processes, the 1,3-dicarboxy-5-halobenzene may be dissolved directly in a certain organic solvent. The certain organic solvent includes dimethylsulfoxide, N,N-dimethylformamide, N,N-dimethylacetamide, N-methylpyrrolidone, etc. Because of their water-miscible property, both these solvents alone and their mixture with water can be used as a reaction solvent.

If the carboxyl groups of the 1,3-dicarboxy-5-halobenzene have been converted into an alkaline salt considering solubility, the tetrasubstituted carboxylic acid produced by dehalogenation condensation is also an alkaline salt. In this case, the treatment thereof with any of various acids, particularly an inorganic strong acid provides 3,5,3',5'-biphenyltetracarboxylic acid.

Hereunder mention will be made of the examples of the present invention.

Example 1

A 6.37-g portion of trimesic acid and 500 g of ε-caprolactam, both having been well dried beforehand, were placed in a glass vessel, and sealed under vacuum to $10^{-2}$ Torr with a vacuum pump. The sealed vessel was shaken for 2 hours in an oven while heating at 120° C., for melting and homogeneously mixing the trimesic acid and the ε-caprolactam. Then the mixture was allowed to stand to increase its temperature to 250° C., and a polymerization reaction was carried out for 72 hours. Next, the above sealed vessel was cooled and then opened, thereby producing a crude resin of the star-shaped nylon of the present example.

The crude resin referred to above was freezed to a glassy state and then crushed, washed with hot water at 80° C. and filtered to remove unreacted monomer, after which the water was removed by vacuum drying to yield a purified resin of the present example. The star-shaped nylon molecular structure of the purified resin according to the present example was confirmed by the results of determination of the terminal carboxylic group (—COOH) in the molecule and by other means for the confirmation of the structure. (The similar confirmation was also made in other Examples.)

The star-shaped nylon resin of the present example comprises molecules of nylon 6 with 3 polymer chains and having a molecular weight of about 13,200.

Samples of the aforementioned purified resin of Example 1 were subjected to tensile tests according to ASTM D638M, to evaluate the tensile strength, tensile modulus and tensile elongation thereof. The results are shown in Table 1.

comprises molecules of nylon 6 with 4 polymer chains and having a molecular weight of about 13,350.

Samples of the aforementioned purified resin of Example 3 were subjected to tensile tests according to ASTM D638M, to evaluate the tensile strength, tensile modulus and tensile elongation thereof. The results are shown in Table 1.

Samples of the aforementioned purified resin of Example 1 were measured for their melt viscosities at 230° C. and 240° C., using a capillary rheometer (capirograph) manufactured by Toyo, Inc., with a die having a diameter of 1 mm. The results are shown in FIGS. 1 and 2, respectively.

Example 4

In the same manner as in Example 1 except that the 500 g of ε-caprolactam was replaced by 810 g of 2-azacyclododecanone, Example 4 was carried out to yield a purified resin of star-shaped nylon. The star-shaped nylon resin of the present example comprises molecules of nylon 11 with 3 polymer chains and having a molecular weight of about 21,000.

Samples of the aforementioned purified resin of Example 4 were subjected to tensile tests according to ASTM D638M, to evaluate the tensile strength, tensile modulus and tensile elongation thereof. The results are shown in Table 1.

Example 5

TABLE 1

|  | Example 1 | Example 2 | Example 3 | Example 4 | Example 5 | Comparison 1 |
| --- | --- | --- | --- | --- | --- | --- |
| Tensile strength (kg/cm$^2$) | 625 | 523 | 613 | 530 | 470 | 621 |
| Tensile modulus (kg/cm$^2$) | 6700 | 5100 | 7340 | 4300 | 3300 | 8910 |
| Tensile elongation (%) | 57 | 25 | 99 | >200 | >200 | 137 |

Samples of the aforementioned purified resin of Example 1 were measured for their melt viscosities at 230° C. and 240° C., using a capillary rheometer (capirograph) manufactured by Toyo, Inc., with a die having a diameter of 1 mm. The results are shown in FIGS. 1 and 2, respectively.

Example 2

In the same manner as in Example 1 except that the amount of trimesic acid was changed to 10.5 g, Example 2 was carried out to yield a purified resin of star-shaped nylon. The star-shaped nylon resin of the present example comprises molecules of nylon 6 with 3 polymer chains and having a molecular weight of about 8,300.

Samples of the aforementioned purified resin of Example 2 were subjected to tensile tests according to ASTM D638M, to evaluate the tensile strength, tensile modulus and tensile elongation thereof. The results are shown in Table 1.

Example 3

In the same manner as in Example 1 except that the 6.37 g of trimesic acid was replaced by 11.0 g of 3,5,3',5'-biphenyltetracarboxylic acid, Example 3 was carried out to yield a purified resin of star-shaped nylon. The star-shaped nylon resin of the present example In the same manner as in Example 1 except that the 500 g of ε-caprolactam was replaced by 872 g of 2-azacyclododecanone, Example 5 was carried out to yield a purified resin of star-shaped nylon. The star-shaped nylon resin of the present example comprises molecules of nylon 12 with 3 polymer chains and having a molecular weight of about 22,000.

Samples of the aforementioned purified resin of Example 5 were subjected to tensile tests according to ASTM D638M, to evaluate the tensile strength, tensile modulus and tensile elongation thereof. The results are shown in Table 1.

Comparison 1

For comparison, samples of the conventional nylon 6 (comprising molecules of linear nylon with a molecular weight of about 13,000) were subjected to tensile tests according to ASTM D638M, to evaluate the tensile strength, tensile modulus and tensile elongation thereof. The results are shown in Table 1.

In addition, samples of Comparison 1 were measured for their melt viscosities at 230° C. and 240° C., using a capillary rheometer (capirograph) manufactured by Toyo, Inc., with a die having a diameter of 1 mm. The results are shown in FIGS. 1 and 2, respectively.

Evaluation of Examples 1–5

As is clearly shown in Table 1, the star-shaped nylon of each of the examples of the present invention, with a molecular weight per polymer chain in the nylon molecule being only ¼–⅓ of that of the linear nylon in Comparison 1, exhibited tensile strength, tensile modulus and tensile elongation not being much different from those of Comparison 1.

As FIGS. 1 and 2 show apparently, the star-shaped nylons of Examples 1 and 3 have melt viscosities at 230° C. and 240° C. being lower than those of the linear nylon of Comparison 1 almost by one figure.

Example 6

In the same manner as in Example 1 except that the trimesic acid was replaced by 1.04 g of tetrakis(4-carboxyphenyl)porphyrin, and the amount of ε-caprolactam was changed into 17.13 g, polymerization and purification were carried out to yield a star-shaped nylon with 4 chains and a porphyrin ring as the core, which had a molecular weight of about 12,800.

Example 7

In the same manner as in Example 1 except that the trimesic acid was replaced by 0.876 g of tetrakis(carboxyphthalocyaninate)Fe(II), and the amount of ε-caprolactam was changed into 20.00 g, polymerization and purification were carried out to yield a star-shaped nylon with 4 chains and a phthalocyanine ring (Fe) as the core, which had a molecular weight of about 15,300.

Example 8

In the same manner as in Example 1 except that the trimesic acid was replaced by 0,879 g of tetrakis(carboxyphthalocyaninate)Ni(II), and the amount of ε-caprolactam was changed into 20.00 g, polymerization and purification were carried out to yield a star-shaped nylon with 4 chains and a phthalocyanine ring (Ni) as the core, which had a molecular weight of about 15,100.

Tensile tests

Samples of the respective purified nylons of Examples 6–8 were subjected to tensile tests according to ASTM D638M, to evaluate the tensile strength, tensile modulus and tensile elongation thereof. The results are shown in Table 2.

TABLE 2

|  | Example 6 | Example 7 | Example 8 |
|---|---|---|---|
| Tensile strength (kg/cm$^2$) | 644 | 620 | 650 |
| Tensile modulus (kg/cm$^2$) | 7230 | 6710 | 6540 |
| Tensile elongation (%) | 67 | 50 | 50 |

Measurement of Melt Viscosities

Samples of the respective purified star-shaped nylons of Examples 6–8 were measured for their melt viscosities at 230° C., using a capillary rheometer (capirograph) manufactured by Toyo, Inc., with a projecting die having a diameter of 1 mm. The shear rate used here was $1.217 \times 10^3$ (1/sec). The results of measurement are shown in Table 3.

TABLE 3

|  | Example 6 | Example 7 | Example 8 |
|---|---|---|---|
| Melt viscosity (poise) | 200 | 305 | 298 |

Evaluation of Examples 6–8

As is clearly shown in Table 2, the star-shaped nylon of Examples 6–8, with a molecular weight per polymer chain in the nylon molecule being only ¼–⅓ of that of the linear nylon in Comparison 1, exhibited tensile strength, tensile modulus and tensile elongation not being much different from those of Comparison 1.

As is clearly shown in Table 3, the star-shaped nylons of Examples 6–8 have melt viscosities at 230° C. being lower than those of the linear nylon of Comparison 1 almost by one figure.

Measurement of Glass Transition Temperatures

The star-shaped and linear nylons of Examples 1, 3, 6, 7 and 8 and Comparison 1 were measured for their dynamic visco-elasticities with a visco-elasticity spectrometer VES-F manufactured by Iwamoto Seisakusho, Inc., to determine the glass transition temperatures thereof. The results are shown in Table 4.

TABLE 4

|  | Exmaple 1 | Example 3 | Example 6 | Example 7 | Example 8 | Comparison 1 |
|---|---|---|---|---|---|---|
| Glass transition temperature (°C.) | 70 | 72 | 84 | 80 | 72 | 65 |

As is apparently shown in Table 4, the star-shaped nylons of Examples 1, 3, 6, 7 and 8 have higher glass transition temperatures or an index of thermal stability, than the linear nylon of Comparison 1.

Example 9

In this example, the polymerization core used in Example 3 or the 3,5,3',5'-biphenyltetracarboxylic acid represented by Formula 1 was synthesized as described hereunder.

A 51.0-g portion of 1,3-dicarboxy-5-bromobenzene was dissolved in a solution of 33.3 g of sodium hydroxide and 120 ml of water, followed by addition of 0.330 g of PdCl$_2$.2NaCl to the solution, after which the temperature was increased to 90° C. In the course of temperature-increasing, a solution of 30 ml of water, 6.66 g of methanol and 9.57 g of formic acid was added dropwise to the mixture over a period of 1 hour. After the completion of the addition, the mixture was stirred for 4 hours while keeping the temperature at 90° C.

After the above-mentioned reaction was over, the Pd was filtered off, and 100 ml of water was added to the filtrate, followed by addition of 90 g of 36% hydrochloric acid solution while cooling with ice, thereby precipitating a white solid. This white solid was filtered off from the liquid phase and purified by recrystallization operation with N,N-dimethylformamide. The yield was 13.0 g (38.0%).

The white crystals mentioned above were confirmed to have the chemical structure represented by Formula 1 by measurement of $^1$H-NMR and IR and by elementary analysis thereof. The results showed that the product is a novel compound not reported so far, so the present inventors named it 3,5,3',5'-biphenyltetracarboxylic acid according to the nomenclature of IUPAC (International Union of Pure and Applied Chemistry).

What is claimed is:

1. A star-shaped nylon with polymer chains emanating from 3 or more polymerization initiation groups which are substituents bonded to every other or more separated carbon atoms on an aromatic ring of an aromatic compound.

2. The star-shaped nylon of claim 1 wherein the aromatic ring of an aromatic compound is one selected from the group consisting of benzene ring, naphthalene ring, anthracene ring, pyridine ring, pyrrole ring, indole ring, furane ring, thiophene ring, purine ring, quinoline ring, phenanthrene ring, porphyrin ring, phthalocyanine ring and naphthalocyanine ring.

3. The star-shaped nylon of claim 1 wherein the aromatic ring of an aromatic compound is composed of at least two rings selected from the group consisting of benzene ring, naphthalene ring, anthracene ring, pyridine ring, pyrrole ring, indole ring, furane ring, thiophene ring, purine ring, quinoline ring, phenanthrene ring, porphyrin ring, phthalocyanine ring and naphthalocyanine ring, said at least two rings being combined together, with or without condensation.

4. The star-shaped nylon of claim 1 wherein the aromatic compound is selected from the group consisting of 1,3,5-benzenetricarboxylic acid (trimesic acid);

3,5,3',5'-biphenyltetracarboxylic acid;
   2,4,6-pyridinetricarboxylic acid;
   3,5,3',5'-bipyridyltetracarboxylic acid;
   1,3,5,7-naphthalenetetracarboxylic acid;
   1,3,6,8-acridinetetracarboxylic acid;
   3,5,3',5+-benzophenonetetracarboxylic acid;

5. The star-shaped nylon of claim 1 wherein the aromatic compound is a porphyrin selected from the group consisting of tetracarboxyphenylporphyrin, aluminum tetracarboxyporphyrin, titanium tetracarboxyporphyrin, nickel tetracarboxyporphyrin and rhodium tetracarboxyporphyrin.

6. The star-shaped nylon of claim 1 wherein the aromatic compound is a phthalocyanine selected from the group consisting of tetracarboxyphthalocyanine, chloro(tetracarboxyphthalocyaninate)aluminum, (tetracarboxyphthalocyaninate)cobalt, (tetracarboxyphthalocyaninate)copper, (tetracarboxyphthalocyaninate)nickel, (tetracarboxyphthalocyaninate)iron, (tetracarboxyphthalocyaninate)oxovanadium, (tetracarboxyphthalocyaninate)lead, (tetracarboxyphthalocyaninate)magnesium, (tetracarboxyphthalocyaninate)tin, and (tetracarboxyphthalocyaninate)zinc.

7. The star-shaped nylon of claim 1 wherein the aromatic compound is a naphthalocyanine selected from the group consisting of tetracarboxynaphthalocyanines and metallic tetracarboxynaphthalocyanines.

8. The star-shaped nylon of claim 1 wherein a monomer for the polymer chains of the nylon is a monomer selected from the group consisting of valerolactam, caprolactam, 2-azacyclododecanone, 2-azacyclotridecanone and 1,8-diazacyclotetradecane-2,7-dione, 9. The star-shaped nylon of claim 1 wherein the polymerization initiation group is a carboxyl group.

10. The star-shaped nylon of claim 1 having a number average molecular weight in the range of 5,000–50,000.

11. The star-shaped nylon of claim 1 having a number average molecular weight in the range of 10,000–30,000.

12. A method for the preparation of a star-shaped nylon, which comprises
   preparing an aromatic compound substituted with 3 or more polymerization initiation groups for initiating polymerization of nylon monomers, which are bonded to every other or more separated carbon atoms on an aromatic ring of the aromatic compound,
   homogeneously mixing the aromatic compound with lactam monomer under a condition where other polymerization initiators for nylon monomers are excluded, and
   polymerizing the nylon monomer starting at the respective polymerization initiation groups of the aromatic compound as the polymerization starting points.

13. The method of claim 12, comprising polymerizing under vacuum.

14. The method of claim 12, comprising polymerizing in a sealed tube.

15. The star-shaped nylon of claim 1 wherein the polymer chains are directly bonded to every other or more separated carbon atoms on an aromatic ring of an aromatic compound.

16. The star-shaped nylon of claim 1 wherein the aromatic compound is selected from the group consisting of
   1,3,5-triaminobenzene;
   1,3,5-tri(aminomethyl)benzene;
   3,5,3',5'-tetraaminobiphenyl;
   2,4,6-triaminopyridine;
   3,5,3',5'-tetraaminobipyridine;
   1,3,5,7-tetraaminonaphthalene;
   1,3,6,8-tetraaminoacridine; and
   3,5,3',5'-tetraaminobenzophenon.

17. The star-shaped nylon of claim 1 wherein the polymerization initiation group is an amino group.

* * * * *